(12) United States Patent
Cantor et al.

(10) Patent No.: US 7,364,888 B2
(45) Date of Patent: *Apr. 29, 2008

(54) INTRATRACHEAL ADMINISTRATION OF LYSOZYME WITH OTHER THERAPEUTIC AGENTS IN THE PREVENTION AND TREATMENT OF RESPIRATORY DISORDERS

(76) Inventors: Jerome Owen Cantor, 258 82nd St., Brooklyn, NY (US) 11209; Bronislava Shteyngart, 258 82nd St., Brooklyn, NY (US) 11209

( * ) Notice: Subject to any disclaimer, the term of this patent is extended or adjusted under 35 U.S.C. 154(b) by 30 days.

This patent is subject to a terminal disclaimer.

(21) Appl. No.: 11/175,332

(22) Filed: Jul. 7, 2005

(65) Prior Publication Data

US 2005/0271645 A1    Dec. 8, 2005

Related U.S. Application Data

(63) Continuation-in-part of application No. 09/826,731, filed on Apr. 5, 2001, now Pat. No. 6,776,989.

(51) Int. Cl.
*C12N 9/00* (2006.01)
(52) U.S. Cl. .................................... 435/183
(58) Field of Classification Search ............... None
See application file for complete search history.

(56) References Cited

U.S. PATENT DOCUMENTS 4,855,227 A * 8/1989 McGarrity et al. ........ 435/7.32
5,993,809 A * 11/1999 Weaver et al. ........... 424/94.61

* cited by examiner

*Primary Examiner*—Michael Meller

(57) ABSTRACT

The subject invention is directed to the prevention and treatment of respiratory disorders by intratracheal administration of an effective amount of lysozyme, either alone or in combination with other therapeutic agents. Applicable respiratory disorders include, but are not limited to, pulmonary emphysema, asthma, bronchitis, pneumonia, respiratory distress syndrome, bronchopulmonary dysplasia, interstitial fibrosis, cystic fibrosis, and neoplasia. The method is intended for a variety of mammals, including humans ranging from premature neonates to adults.

4 Claims, No Drawings

INTRATRACHEAL ADMINISTRATION OF LYSOZYME WITH OTHER THERAPEUTIC AGENTS IN THE PREVENTION AND TREATMENT OF RESPIRATORY DISORDERS

RELATED APPLICATIONS

This application is a continuation-in-part of U.S. Pat. No. 6,776,989, which was issued on Aug. 17, 2004 (Examiner Michael Meller, Art Unit 1654). The applicants claim benefit of provisional application No. 60/585,074, filed on Jul. 6, 2004.

BACKGROUND OF THE INVENTION

Lysozyme is increased in inflammatory reactions and is a component of the extracellular matrix, but its possible role in lung diseases such as emphysema and interstitial fibrosis has not been investigated. Determining the significance of any changes in pulmonary lysozyme content is complicated by the fact that this protein has no recognized physiological function in the lung other than protecting it from bacterial infection (1-3).

To further understand the role of lysozyme in pulmonary disease, tissue sections from normal, fibrotic, and emphysematous human lungs were evaluated for differences in lysozyme content. An increase in extracellular lysozyme was specifically observed in lung tissues with pulmonary emphysema, and the protein was preferentially associated with elastic fibers, which undergo breakdown in this disease (4).

Since this laboratory and other investigators have previously shown that hyaluronan and other polysaccharides surround elastic fibers (5-7), normal lung tissues were treated with hyaluronidase and examined for their ability to bind exogenously administered lysozyme. Such treatment resulted in increased attachment of lysozyme (4), suggesting that degradation of extracellular matrix components, as occurs in pulmonary emphysema, may expose binding sites for lysozyme on elastic fibers. In vitro studies, using an extracellular matrix preparation mainly composed of elastic fibers, confirmed that lysozyme has a strong affinity for these fibers (unpublished observations).

While the mechanism responsible for the observed affinity of lysozyme for elastic fibers is unclear, it is possible that lysozyme may bind to specific carbohydrate residues in elastic fibers. N-acetyl-D-glucosamine, a component of bacterial cells susceptible to degradation by lysozyme, has also been found in glycoproteins associated with elastic fibers (8). Injury to elastic fibers, as occurs in pulmonary emphysema, may expose such residues, thereby facilitating lysozyme binding.

The enhanced binding of lysozyme to elastic fibers in pulmonary emphysema may protect these fibers from further injury. Previous work by other investigators has shown that lysozyme prevents elastolysis in vitro (9). Lysozyme could therefore be useful in treating emphysema and other diseases involving damage to elastic fibers, such as asthma, pulmonary fibrosis, respiratory distress syndrome, bronchopulmonary dysplasia, and cystic fibrosis. This protective effect of lysozyme would complement its antibacterial properties (1-3) and make it particularly beneficial in the treatment of certain types of pulmonary infections where there is necrotizing lung injury. Similarly, lysozyme has been reported to counteract HIV infection (10) and may therefore be useful in the treatment of pneumonias and other disorders associated with AIDS.

Another useful property of lysozyme is its ability to bind to and disaggregate hyaluronan and other polyanionic compounds (11). Lysozyme might therefore be utilized to treat lung diseases involving excess mucus secretion in airways. In particular, this protein may help alleviate the obstruction of airways associated with pneumonias, asthma, and cystic fibrosis.

This same ability of lysozyme to disaggregate hyaluronan may also be beneficial in pulmonary fibrosis, where significant accumulation of this polysaccharide occurs in combination with collagen, elastin and other polysaccharides (12-14). By disaggregating hyaluronan, lysozyme may interfere with the fibrotic process, thereby ameliorating the disease. As shown in studies from this laboratory (4), there is a decrease in lung lysozyme content in pulmonary fibrosis (relative to the proliferation of other tissue components), which may conceivably facilitate the fibrotic response.

With regard to intratracheal administration of lysozyme, this laboratory has shown that an aerosol preparation of the protein rapidly penetrates the lung, remains there for at least 24 hrs, and does not cause pulmonary injury (15). These findings suggest that lysozyme could also act as a vehicle for intratracheal delivery of drugs for the treatment of pulmonary and systemic diseases. By virtue of its attachment to elastic fibers, lysozyme could slow the pulmonary clearance of inhaled therapeutic agents, thereby increasing their effectiveness in the lung.

To date, the use of intratracheally instilled lysozyme as an adjunct to conventional antibiotic therapy has been limited to the administration of the antibiotic via routes other than intratracheal instillation (16). The disadvantages of this type of combined therapy are: 1) reduced concentration of the antibiotic in the lung due to systemic dilution; 2) the inability of lysozyme to interact with and potentiate maximal dosages of the antibiotics due to separate routes of administration (e.g. intratracheal lysozyme with oral carbenicillin); 3) different clearance rates of lysozyme and antibiotic from the lung, resulting in a loss of interaction time between the two agents.

In contrast, the combined intratratracheal administration of lysozyme with antibiotics (and other treatment agents) takes advantage of their common anatomical and temporal associations within the lung. This form of administration should maximize the effects of the particular therapeuctic agent combined with lysozyme. For example, intratracheal administration of lysozyme with an antibiotic such as rifampin (whose site of action is within the cytoplasm of the pathogenic organism) would allow more rapid penetration of the antibiotic into the organism due to the cell wall-lytic effect of lysozyme. Maximal synergy between the two agents is dependent on their presence in the lung at the same time and place, which is only possible by their combined intratracheal administration.

The novelty of this approach is made apparent by the fact that previous attempts to combine lysozyme with antibiotics were based solely on the potential for lysozyme to stimulate the systemic immune system, not potentiate the effect of the antibiotic per se. Therefore, the need to intratracheally administer lysozyme in combination with the antibiotic was not perceived as advantageous by one skilled in the art. Further evidence of the novelty of this approach is provided by the fact that such combined intratracheal administration of lysozyme and antibiotics (or other therapeuctic agents)

has not been attempted despite the availability of lysozyme for therapeutic use over the past half-century.

The possibility that lysozyme may be effective against pathogenic organisms in vivo has only been described very recently, subsequent to the filing of the initial patent (U.S. Pat. No. 6,776,989) by the applicants on Apr. 5, 2001.

DETAILED DESCRIPTION OF THE INVENTION

The subject invention is directed to the prevention and treatment of respiratory disorders by intratracheal administration of an effective amount of lysozyme, either alone or in combination with other therapeutic agents. Applicable respiratory disorders include, but are not limited to, pulmonary emphysema, asthma, bronchitis, pneumonia, respiratory distress syndrome, bronchopulmonary dysplasia, interstitial fibrosis, cystic fibrosis, and neoplasia. The method is intended for a variety of mammals, including humans ranging from premature neonates to adults.

The supplementation of known pulmonary therapeutic agents with lysozyme is designed to potentiate the activity of the therapeutic agent(s), thus making it more effective against the disease process for which it is intended. For example, lysozyme might be added to an antibiotic to increase its ability to kill bacteria. Likewise, lysozyme might be added to surfactant to prolong its useful effects in the lung and to prevent infection.

Furthermore, lysozyme may be administered intratracheally as a prophylaxis for respiratory disorders such as pneumonia. For example, lysozyme might be given to neonates in the respiratory intensive care unit to prevent development of pneumonia. This might be particularly useful in reducing the subsequent need for treatment with antibiotics that may be ineffective against certain strains of bacteria that have developed resistance to the antibiotics.

Administration of lysozyme with or without additional therapeutic agents may be performed by aerosol, which can be generated by a nebulizer, or by instillation. The lysozyme may be administered alone or with a carrier such as saline solution, DMSO, an alcohol, or water. The lysozyme may be isolated from a natural source, such as eggs, or synthesized by a bioprocess, such as fermentation. The effective daily amount of lysozyme is from about 10 µg/kg to about 1 mg/kg of body weight.

The amount of lysozyme intratracheally administered daily to a human being may vary from about 10 µg/kg to about 1 mg/kg of body weight. Preferably, the daily amount is from about 10 µg/kg to about 100 µg/kg, for example about 50 µg/kg body weight of the human being treated (daily). The intratracheal lysozyme may be administered in any of the methods well known to those skilled in the art. For example, the lysozyme may be administered in the form of an aerosol or may be administered by instillation. If administered in the form of an aerosol, a nebulizer is used to produce lysozyme in aerosol form (See for example U.S. Pat. Nos. 4,649,911 and 4,119,096).

Typically, the lysozyme is administered in a pharmaceutically acceptable carrier. Such examples include saline solution, DMSO, alcohol, or water. Such carriers are well known in the art, and the specific carriers employed may be varied depending upon factors such as size of the subject being treated, treatment dose, and the like.

When administered in combination with other therapeutic agents, both the lysozyme and the other agent(s) may be similarly combined with a pharmaceutically acceptable carrier such as DMSO, alcohol, or water. The agent given in combination with lysozyme would be administered at a dosage that is therapeutically effective, based on studies that are well-known to the art.

Antibiotics to be given in combination with lysozyme include Ampicillin, Sulbactam, Cefotaxime, Ceftriaxone, Cefepime, Imipenem, Meropenem, Piperacillin, Tazobactam, Azithromycin, Clarithromycin, Erythromycin, Vancomycin, Clindamycin, Gatofloxicin, Levofloxacin, Moxifloxacin, Ciprofloxacin, Tobramycin, Gentamicin, Amikacin, Doxycycline, Aztreonam, and Pentamidine.

Naturally occurring antimicrobial substances to be given in combination with lysozyme include lactoferrin, secretory leukoprotease inhibitor (SLPI), and beta-defensins.

Surfactant proteins (SP) to be given in combination with lysozyme include SP-A, SP-B, SP-C, and SP-D.

Synthetic surfactants to be given in combination with lysozyme include Curosurf®, Exosurf®, Surfaxin®, and Survanta®.

The time over which the lysozyme (with or without additional therapeutic agent) is administered may vary as is well-known in the art to achieve the desired results. For example, the lysozyme with or without additional therapeutic agents may be administered as an aerosol from about 10 minutes to about 1 hour per treatment regimen, 3 times daily, or until the desired daily dosage is fully administered.

In addition, forms of lysozyme may be derived from the eggs of chickens and other species, or synthesized by a bioprocess, such as fermentation. All forms of lysozyme, regardless of source, would follow a treatment similar to that described above.

REFERENCES

1. Agerberth B, Grunewald J, Castanos-Velez E, Olsson B, Jornvall H, Wigzell H, Eklund A, Gudmundsson G H. Antibacterial components in bronchoalveolar lavage fluid from healthy individuals and sarcoidosis patients. Am J Respir Crit Care Med July 1999;160(1):283-90.
2. Travis S M, Conway B A, Zabner J, Smith J J, Anderson N N, Singh P K, Greenberg E P, Welsh M J. Activity of abundant antimicrobials of the human airway. Am J Respir Cell Mol Biol May 1999;20(5):872-9.
3. Schnapp D, Harris A. Antibacterial peptides in bronchoalveolar lavage fluid. Am J Respir Cell Mol Biol September 1998;19(3):352-6.
4. Shteyngart B, Chaiwiriyakul S, Wong J, Cantor J O. Preferential binding of lysozyme to elastic fibers in pulmonary emphysema. Thorax 53:193-196, 1998.
5. Cantor J O, Cerreta J M, Armand G, Turino G M. Further investigation of the use of intratracheally administered hyaluronan to ameliorate elastase-induced emphysema. Exp Lung Res 1997; 23:229-44.
6. Baccarani-Contri M, Vincenzi D, Cicchetti F, Mori G, Pasquali-Ronchetti I. Immunocytochemical localization of proteoglycans within normal elastin fibers. Eur J Cell Biol 1990;53:30-512.
7. Baccarani-Contri M, Fornieri C, Pasquali-Ronchetti I. Elastin-proteoglycans association revealed by cytochemical methods. Conn Tissue Res 13:237-249, 1985.
8. Amaya J. The effect of steroids on organ-cultured porcine trabecular meshwork: an ultrastructural, biochemical, and lectin histochemical study. Acta Societatis Opthalmologicae Japonicae 1995;99:995-1004.
9. Park P W, Diedermann K, Mecham L, Bissett D L, Mecham R P. Lysozyme binds to elastin and protects elastin from elastase-mediated dgradation. J Invest Dermatol 1996;106:1075-1080.

10. Lee-Huang S, Huang P L, Sun Y, Huang P L, Kung H F, Blithe D L, Chen H C. Lysozyme and RNases as anti-HIV components in beta-core preparations of human chorionic gonadotropin. Proc Natl Acad Sci USA 1999;96:2678-81.
11. Van Damme M P, Moss J M, Murphy W H, Preston B N. Binding properties of glycosaminoglycans to lysozyme-effect of salt and molecular weight.
Arch Biochem Biophys 1994;310:16-24.
12. Zhao H W, Lu C J, Yu R J, Hou X M. An increase in hyaluronan by lung fibroblasts: a biomarker for intensity and activity of interstitial pulmonary fibrosis? Respirology 1999; 4(2):131-8.
13. Gerdin B, Hallgren R. Dynamic role of hyaluronan (HYA) in connective tissue activation and inflammation. J Intern Med 1997;242(1):49-55.
14. Cantor J O, Cerreta J M, Osman M, Mott S H, Mandl I, Turino GM. Glycos-aminoglycan synthesis in bleomycin-induced pulmonary fibrosis: Biochemistry and autoradiography. Proc Soc Exp Biol Med 1983;174:172-181.
15. Cantor J O, Shteyngart B, Cerreta J M, Turino G M. The effect of lysozyme on elastase-mediated injury. Exper Biol Med 227:108-113, 2002.
16. Luniakin A A, Bogomaz T A. Lysozyme in the overall treatment of children with influenza infection and pneumonia. Pediatr Akus Ginekol January-February (1):11-13, 1977 (Ukrainian).

What is claimed is:

1. A method of treating pneumonia in a mammal that consists of intratracheally administering to the lung of the mammal a therapeutically effective amount of lysozyme in combination with other antimicrobial agents.

2. A method of claim 1, wherein the mammal is a human.

3. A method of claim 1, wherein the lysozyme is produced by a bioprocess, using plants or animals.

4. A method of claim 1, wherein the antimicrobial agents given in combination with lysozyme are selected from the group consisting of Ampicillin, Sulbactam, Cefotaxime, Ceftriaxone, Cefepime, Imipenem, Meropenem, Piperacillin, Tazobactam, Azithromycin, Clarithromycin, Erythromycin, Vancomycin, Clindamycin, Gatofloxicin, Levofloxacin, Moxifloxacin, Ciprofloxacin, Tobramycin, Gentamicin, Amikacin, Doxycycline, Aztreonam, Pentamidine, Lactoferrin, Secretory Leukoprotease Inhibitor, and Beta-Defensins.

* * * * *